United States Patent [19]
Biermann et al.

[11] Patent Number: 5,374,716
[45] Date of Patent: Dec. 20, 1994

[54] PROCESS FOR THE PRODUCTION OF SURFACE ACTIVE ALKYL GLYCOSIDES

[75] Inventors: Manfred Biermann, Muelheim; Karlheinz Hill, Erkrath; Willi Wuest, Ratingen; Rainer Eskuchen, Duesseldorf-Benrath; Josef Wollmann, Herzogenrath; Andreas Bruns, Langenfeld; Guenter Hellmann, Hilden; Karl-Heinz Ott, Erkrath; Walter Winkle, Monheim; Klaus Wollmann, Haan, all of Germany

[73] Assignee: Henkel Kommanditgesellschaft auf Aktien, Duesseldorf, Germany

[21] Appl. No.: 517,955

[22] Filed: Apr. 27, 1990

Related U.S. Application Data

[63] Continuation of Ser. No. 220,297, Jul. 18, 1988, abandoned.

[30] Foreign Application Priority Data

Jul. 18, 1987 [DE] Germany .................. 3723826

[51] Int. Cl.$^5$ .................. C07H 1/00; C07H 15/10; C08B 31/10
[52] U.S. Cl. .................. 536/18.6; 536/18.5; 536/124
[58] Field of Search .................. 536/18.5, 18.6, 4.1, 536/124, 127, 119

[56] References Cited

U.S. PATENT DOCUMENTS

| | | |
|---|---|---|
| 3,450,690 | 6/1969 | Gibbons et al. .................. 260/210 |
| 3,547,828 | 12/1970 | Mansfield et al. .................. 252/351 |
| 3,974,138 | 8/1976 | Lew .................. 536/4 |
| 4,393,203 | 7/1983 | Mao et al. .................. 536/124 |
| 4,483,979 | 11/1984 | Mao .................. 536/18.6 |
| 4,557,729 | 12/1985 | McDaniel, Jr. et al. .................. 8/111 |
| 4,704,453 | 10/1987 | Lorenz et al. .................. 536/18.6 |
| 4,713,447 | 12/1987 | Letton .................. 536/18.6 |
| 4,797,478 | 1/1989 | Lebuhn et al. .................. 536/18.5 |
| 4,820,814 | 4/1989 | Lueders .................. 536/127 |

FOREIGN PATENT DOCUMENTS

| | | |
|---|---|---|
| 1353333 | 11/1983 | Austria . |
| 1209990 | 5/1983 | Canada . |
| 1227793 | 1/1987 | Canada . |
| 0092875 | 11/1983 | European Pat. Off. . |
| 096917 | 12/1983 | European Pat. Off. . |
| 132043 | 1/1985 | European Pat. Off. . |
| 132046 | 1/1985 | European Pat. Off. . |
| 0132046 | 1/1985 | European Pat. Off. . |
| 593422 | 2/1934 | Germany . |
| 611055 | 2/1935 | Germany . |

*Primary Examiner*—John W. Rollins
*Assistant Examiner*—Gary L. Kunz
*Attorney, Agent, or Firm*—Ernest G. Szoke; Wayne C. Jaeschke; Real J. Grandmaison

[57] ABSTRACT

A process for the production of surface-active alkyl glycosides which is carried out by the transacetalization method with butanol, leads to a new alkyl glycoside as end product which is characterized by high color-stability in alkaline medium; besides a high proportion of alkyl monoglycoside, the product also contains polyglycoside on polyglycose and butyl glucoside.

16 Claims, No Drawings

PROCESS FOR THE PRODUCTION OF SURFACE ACTIVE ALKYL GLYCOSIDES

This is application is a continuation of application Ser. No. 07/220,297 filed Jul. 18, 1988, now abandoned.

BACKGROUND OF THE INVENTION

1. Field of the Invention

This invention relates to a process for the production of surface active alkyl glycosides by reacting butanol with a glycose in the presence of a suitable acid catalyst to form a butyl glycoside. The butyl glycoside is then transacetalized with a fatty alcohol containing from 12 to 18 carbon atoms. The products of this invention are surface active and show good biodegradability.

2. Statement of Related Art

In the development of new surface-active substances, which are suitable for use as industrial surfactants for the manufacture of detergents and cleaning preparations, renewable raw materials are being used to an increasing extent for production. Hitherto, oleochemical raw materials, such as for example fatty acids, fatty acid esters and fatty alcohols, have largely been used for this purpose. The object of the efforts being made in this direction is to develop a base independent of petrochemistry and, at the same time, to obtain better products showing environmental compatibility, including good biological degradability. With these aspects in mind, interest has recently been shown in the surface-active alkyl glycosides, which are acetals of sugars and fatty alcohols.

In the context of the invention, alkyl glycosides are understood to be the reaction products of sugars and fatty alcohols, suitable sugar components being the aldoses and ketoses glucose, fructose, mannose, galactose, talose, gulose, allose, altrose, idose, arabinose, xylose, lyxose and ribose, which are referred to hereinafter as glycoses. Particularly preferred alkyl glycosides are alkyl glucosides by virtue of the ready availability of glucose. In its broadest sense, the term "alkyl" in alkyl glycoside is intended to encompass the residue of an aliphatic alcohol, preferably a fatty alcohol, obtainable from natural fats, i.e. saturated and unsaturated residues and also mixtures thereof, including those having different chain lengths. The terms alkyl oligoglycoside, alkyl polyglycoside, alkyl oligosaccharide and alkyl polysaccharide apply to alkylated glycoses of the type in which one alkyl radical in the form of the acetal is attached to more than one glycose residue, i.e. to a polysaccharide or oligosaccharide residue; these terms are regarded as synonymous with one another. Accordingly, alkyl monoglycoside is the acetal of a monosaccharide. Since the reaction products of the sugars and the fatty alcohols are generally mixtures, the term alkyl glycoside is intended to encompass both alkyl monoglycosides and also alkyl poly(oligo)glycosides, providing the particular structural differences are not important.

The surface-active alkyl glycosides essentially containing $C_{12}-C_{18}$ alkyl or alkenyl radicals belong to the class of nonionic surfactants. However, whereas in standard nonionic surfactants of the alkyl polyglycol ether type, the hydrophobic part emanates from renewable raw materials where it is derived from fatty alcohols, while the hydrophilic part is made up of ethylene oxide units and hence of a petrochemical raw material, the alkyl glycosides as fatty alkyl glycosides may be completely prepared from renewable raw materials, namely fats on the one hand and sugars or starches on the other hand.

Surface-active alkyl glycosides have been known as ingredients in detergents for more than 50 years. Thus, Austrian patent 135,333 describes the production of lauryl glucoside and cetyl glucoside from acetobromoglucose and the particular fatty alcohol in the presence of a base. The direct synthesis from glucose and lauryl alcohol in the presence of hydrogen chloride as an acidic catalyst is also disclosed.

According to the teaching of German patent 611,055, alkyl glucosides can be prepared from penta-acetyl glucose and a fatty alcohol in the presence of anhydrous zinc chloride.

German patent 593,422 describes the maltosides, the lactosides of aliphatic alcohols containing more than 8 carbon atoms and their use as emulsifying, cleaning and wetting agents. For example, the addition of cetyl maltoside to ordinary soap, which at that time was the principal constituent of detergents, was said to improve the detergent effect of the soap. This is explained by the effect of the cetyl maltoside as a calcium soap dispersant.

The sixties and seventies saw several proposals for improved processes for the production of alkyl glycosides either by direct reaction of glycose, generally in the form of glucose, with an excess of the fatty alcohol and an acid as catalyst (direct synthesis) or using a lower alcohol or glycol as solvent and reactant (transacetalization). Thus, U.S. Pat. No. 3,547,828 (Mansfield et al.) describes the production of a ternary mixture of alkyl oligoglucosides, alkyl monoglucosides and the corresponding $C_{11}-C_{32}$ alkanols by transacetalization with butanol. In this process, the glucose is first reacted with butanol and an acidic catalyst, such as sulfuric acid, to form butyl glucoside. The water of reaction is separated at the reflux temperature. Two to six mols of butanol are used per tool glucose. The fatty alcohol is then added in quantities of 0.5 to 4 tools per mol of glucose and the excess butanol and also the butanol formed during the transacetalization reaction are removed by distillation. The transacetalization reaction is optionally terminated, such that parts of the butyl glycoside remain in the reaction mixture. Products of low viscosity can be prepared in this manner. The acidic catalyst is then neutralized by addition of sodium hydroxide solution. Excess fatty alcohol is then largely removed in vacuo to the required level, generally to less than 2% by weight. For example, lauryl alcohol can thus be removed by distillation under a pressure of 2 mm Hg at a temperature of 150° C. A proportion of alkyl oligoglucoside can be isolated from the resulting 3-component mixture of alkyl monoglucoside, alkyl ol igoglucoside and fatty alcohol, optionally containing proportions of butyl glycoside, by adding acetone to the mixture. The oligoglucosides are insoluble in acetone and can be easily separated.

U.S. Pat. No. 3,450,690 (Gibbons et al.), teaches that unwanted alkali-sensitive, discoloring impurities of alkyl glucosides based on $C_1-C_8$ alkanols, prepared by direct synthesis, can be removed from the reaction product by not only neutralizing the acidic catalyst through its addition of inorganic or organic bases, as for example sodium hydroxide, sodium methylate, calcium hydroxide, barium hydroxide, barium methylate or strongly basic organic amines, but also by adjusting the mixture to an alkaline pH value of at least 8, followed by brief heating to temperatures of 50° C. to 200° C. The reaction product is then filtered off and the excess of alcohol is removed. The residual reducing sugar, which is thought to be responsible for the color instability of the untreated product, are alleged to be removed by this treatment.

Another problem arising in the production of surface-active alkyl glycosides based on fatty alcohols containing 12 to 18 carbon atoms lies in the difficulty of separating any such unreacted fatty alcohols by distillation from the reaction product. To this end, it is proposed in European patent application 32 252 (BASF, Klahr et al.) to effect the separation of such unreacted fatty alcohols by distillation in the presence of glycols having boiling points which are at most 10° C. above and at most 30° C. below those of the alcohols to be separated. In this way, the distillation process can be carried out at temperatures no higher than 140° C. under a vacuum of about 8 mbar.

According to the teaching of European patent application 92 875 (Proctor & Gamble) Mao et al. production of long-chain alkyl glycosides utilizing its transacetalization process with butanol can be controlled in such a way that the end product contains a residue of less than 10% by weight of butyl glucosides. The formation of long-chain alkyl oligoglycosides having a relatively high degree of oligomerization, i.e. containing 6 and more glucose units in the molecule, can also be reduced. The products thus obtained consist essentially of alkyl monoglucoside and alkyl oligoglucosides, the content of alkyl monoglucosides being at most 60% by weight and the average degree of oligomerization being from 1.5 to 3. The proportion of short-chain alkyl glucosides, particularly butyl glucosides, is below 10%, while the proportion of unreacted fatty alcohol is said to be below 2%. The use of a thin-layer evaporator is recommended for the removal of the fatty alcohol by distillation.

European patent application 92 876 (Proctor & Gamble, Mao et al.) also describes the production of long-chain alkyl glucosides having a degree of oligomerization of 1.5 to 20 by the transacetalization process with butanol, the transacetalization catalyst (p-toluenesulfonic acid) being inactivated by neutralization when at least 90% of the butyl glucoside has reacted, such that at most 10% butyl glucoside remains in the reaction product. In this case, too, the use of a thin-layer evaporator is recommended for removal of the excess of fatty alcohol. The reaction products are also said to contain less than 60% by weight alkyl monoglucoside and less than 2% free fatty alcohol, In this known production process, a very small excess of fatty alcohol is used to ensure that large quantities of the required alkyl oligoglucoside, i.e. more than 60% by weight, are obtained.

European patent application 96 917 (Procter & Gamble, Farris) describes an improved process for the acid-catalyzed direct synthesis, in which a monosaccharide, preferably glucose, is added to the mixture of fatty alcohol and catalyst continuously or in portions at a temperature of from 80 to 150° C. at such rate that no more than 10% unreacted monosaccharide is present in the reaction mixture. The addition of the monosaccharide is controlled in such a way that a substantially clear phase is always present.

The monosaccharide is preferably used as finely ground powder in admixture with part of the fatty alcohol. As the monosaccharide is added, the water formed is removed by distillation under a reduced pressure of about 0.1 to 300 mm Hg. This process is said to give a product containing 20 to 70% alkyl monoglycoside, less than 10% mono- and polysaccharides, less than 2% free fatty alcohol and, the remainder being alkyl polyglycosides, i.e. essentially di-, tri- and tetraglycosides.

According to European patent application 132 046 (Procter & Gamble, Letton), an organic base which is either the alkali (Na, K, Li), alkaline earth (Ba, Ca) or aluminum salt of a weak low molecular weight acid, for example sodium acetate, or the corresponding alcoholate, for example sodium ethylate, is used to neutralize the acidic catalyst in a direct synthesis process. A narrow pH value range near the neutral point (pH 6.6 to 7, preferably 6.7 to 6.8) is established.

According to European patent application 132 043 (Procter & Gamble, Davis et al.), the color quality of the product is improved and the residual polysaccharide in the product is reduced when the acidic catalyst used is the acid form of an anionic surfactant. In the process according to this literature reference, 2 mols of fatty alcohol are preferably used per mol of glucose and pH values of 6.6 to 7 are attained by adjustment in the neutralization of the acid catalyst with sodium hydroxide or sodium carbonate.

To be able to use the alkyl glycosides as surfactant ingredients in detergents and cleaning preparations in commercial scale, two requirements have to be satisfied. First, the alkyl glycosides must be color-stable under alkaline conditions so that they can be used in alkaline formulations. Second, processes for the production of alkyl glycosides must be designed in such a way that the end products can be produced without difficulty in large quantities. Neither of these two requirements is satisfied by known processes or by the properties of the resulting end products.

According to European patent application 77,167 (Rohm & Haas, Arnaudis), the color quality of the surface-active alkyl glycosides may be improved by using a standard acid catalyst together with an acidic reducing agent selected from the group comprising phosphorous acid, hypophosphorous acid, sulfurous acid, hyposulfurous acid, nitrous acid and/or hyponitrous acid, or salts thereof, in the production of the alkyl glycosides.

According to the teaching of European patent application 102, 558 (BASF, Lorenz et al.), light-colored $C_3$-$C_5$ alkyl glucosides, which may be transacetalized to higher, surface-active alkyl glucosides, are obtained by production in the presence of an acidic catalyst and at least equivalent quantities of an alkali metal salt of a boric acid, preferably sodium perborate.

According to another proposal in European patent application 165 721 (Staley, McDaniel et al.), an aqueous solution of a surface-active alkyl polyglucoside is treated first with an oxidizing agent, (preferably a hydrogen peroxide solution), and then with a sulfur dioxide source, such as an aqueous solution of sodium bisulfite. The products thus obtained are said to remain color-stable, even after prolonged storage.

All known production processes which are concerned with improving the color quality and stability of alkyl glycosides in storage are attended by the disadvantage that, to achieve these improvements, additional chemical agents have to be added either during the production process or by way of aftertreatment of the reaction product.

DESCRIPTION OF THE INVENTION

Other than in the operating examples, or where otherwise reaction conditions used herein are to be understood as modified in all instances by the term "about".

An object of the present invention is to provide a new process for the production of surface-active alkyl glycosides, in which the end products produced are of such quality that there is no need for aftertreatment to improve color quality and stability in storage.

Another object of the invention is to control the individual steps of the new production process in such a manner that a minimum of chemical reagents is sufficient. Another object of the invention is to provide a process which can be readily applied on an industrial scale, thus enabling surface-active alkyl glycosides to be produced in such quantities that these products may be used by the detergent industry as surfactants in detergents and cleaning preparations.

It has now been found that these and other objects can be achieved by a novel combination of known and novel process features in a general process of the transacetalization type.

In accordance with the present invention it has been found that surface-active alkyl glycosides containing $C_{12}$-$C_{18}$ alkyl or alkenyl radicals are produced by a process which comprises:

1. introducing to a suitable reaction vessel a first portion of butanol together with an acidic catalyst;
2. heating the butanol-acid catalyst mixture to the reflux temperature;
3. adding a suspension of a glycose reactant and the remaining butanol;
4. removing water formed in reaction by distillation;
5. adding to the reaction mixture a fatty alcohol containing from 12 to 18 carbon atoms;
6. removing butanol from the reaction mixture through distillation under reduced pressure, until from 0 to 30 mol percent of butylglycosides per mol glycose remains in the reaction mixture;
7. cooling the reaction mixture to a temperature below 95° C. and neutralizing the acidic catalyst by the addition of a suitable base and then adjusting the pH of the neutralized reaction mixture to a pH of at least 8;
8. filtering the reaction mixture at a temperature of from 80° C. to 90° C., and;
9. Removing excess fatty alcohol by distillation to a level below 5% by weight.

The reaction product thus obtained is processed, preferably in known manner, by addition of water to form an easy-to-handle, approximately 60% paste. The reaction product is yellowish to brownish in color. It has surprisingly been found that the reaction product retains its original color quality to a satisfactory extent in storage and, in particular, even during further processing in an alkaline medium. The product quality directly obtained by the process is entirely adequate for most applications of the alkyl glycoside produced in accordance with the invention for the production of detergents and cleaning preparations. However, color quality and alkali stability may be further improved by subsequent bleach with hydrogen peroxide or an organic per acid, if desired.

The butanol reactant is employed in an amount from 4 mols to 10 mols and preferably from 6 mols to 8 mols per tool of glycose employed.

The butanol is divided into two parts, one for initial addition with the catalyst and, one for later addition with the glycose. It is preferred to suspend the glycose in the butanol for the second addition.

The portions of butanol are each preferably 50% by weight but can be from 30 to 70 and from 70 to 30 weight percent.

The acidic catalyst used is a compound showing an acidic reaction. Preferred acidic catalysts are sulfuric acid, phosphoric acid, p-toluene sulfonic acid and sulfo acid ion exchange resins.

The acid catalyst is preferably used in an amount of from 0.005 to 0.02 tool per tool of the glycose used.

In respect to step 3, it is preferred to heat the glycose butanol suspension to the approximate of reaction mixture prior to addition.

In respect to step 4, it is preferred to remove the water by distillation under slightly reduced pressure. Pressures of from 800 to 950 mbar are preferred. An azeotropic amount of butanol is removed with the water.

In respect to step 5, it is preferred to preheat the alcohol before addition. The temperature is desireably about the same as the reaction mixture to which it will be added.

The fatty alcohol is used in an amount of from 2 mols to 20 mols per mol of glycose. The fatty alcohol is preferably added continuously.

In respect to step 7, suitable bases include organic or inorganic basic materials such as the alkali metal bases such as alkali metal hydroxide, carbonates, bicarbonates and the like, the alkaline earth bases such as calcium oxide magnesium oxide and the like, aluminum bases such as aluminum hydroxide or its basic alkali aluminum components, ammonia compounds, such as ammonium hydroxide, amines including primary, secondary tertiary and heterocyclic amines and the like.

Glucose is preferably used as the glycose in the process according to this invention. Normally, glucose contains 1 mol water of crystallization. Glucose such as this containing water of crystallization may readily be used as starting material in the process according to the invention, although in that case the water of crystallization has also to be removed from the reaction medium. However, since anhydrous glucose is available in large quantities as a starting material, it is particularly preferred to use anhydrous glucose in the form of a fine powder. Para toluene sulfonic acid is preferably used as the acid catalyst by virtue of its lesser corrosive effect - compared with sulfuric acid - on apparatus and pipes made of steel. In principle, however, any acidic compounds, including the so-called Lewis acids, which catalyze the acetalization reaction between fatty alcohol and the sugar molecule, may be used as catalysts.

To remove the water of reaction by distillation immediately after its release, a temperature equilibrium has to be established in the reaction vessel. To this end, the butanol initially introduced into the reaction vessel is brought to the reflux temperature before the reaction with glycose and the distillation column operated with infinite reflux. In the case of the n-butanol used in accordance with the invention, the reflux temperature is 118° C. With the formation of the lower boiling butanol/water mixture, a vapor temperature of 95° to 110° C. is established. After phase separation of the butanol/water distillate, the butanol-rich phase may be returned to the column although it contains dissolved water. However, where the process is carried out on a laboratory scale, it is easier to replace the quantity of water distilled off by fresh butanol. Where the process is carried out on an industrial scale, the water-containing butanol phase may readily be returned to the column where the water of the butanol phase becomes quasi-stationary and no longer comes into contact with the reaction mixture. A light vacuum of 800 to 950 millibar (mbar) may be applied even during the heating of the butanol in order thus to adjust the reflux temperature to the butanol/water vapor temperature.

In applying the heat required to remove the butanol/water mixture and to maintain the reaction temperature, it is essential that there be only a minimal temperature difference between the wall of the reactor and the reaction mixture in order to avoid overheating. In order to establish this slight temperature difference, it is sufficient in the laboratory to use a standard thermostat regulated oil bath and, at the same time, to vigorously stir the reaction mixture. On an industrial scale, it has proved to be of particular advantage to apply the heat through an external circuit, preferably consisting of a pump and a heat exchanger. To this end, part of the reaction mixture is continuously removed through a pipe, heated in the heat exchanger and returned to the reactor. It is possible in this way to avoid high reactor wall temperatures, i.e. those above 125° C., and avoid adverse temperature effects on the color values of the end product.

In one preferred embodiment of the process, the suspension of the glycose in butanol (anhydrous glucose is preferably used) is first treated to produce a fine dispersion. In the laboratory, this can be easily done in a standard, high-speed laboratory stirrer or blender. Alternatively an ultrasonic homogenizer can be used for this purpose. On an industrial scale, an inline mixer, for example a stator/rotor mixer, is advantageously used to produce a fine dispersion. This fine dispersion step has the desirable secondary effect that the suspension undergoes an increase in temperature. The glycose suspension is introduced into the reaction vessel either in portions or continuously. Portion or batchwise addition is an advantage in the laboratory and continuous addition is an advantage for industrial scale. In both cases, the addition rates or the time intervals between the added portions must be selected so that the reaction mixture remains substantially clear, i.e. forms a homogeneous phase. In the context of this invention, this expression is used to mean that a brief period in which the reaction mixture is clouded initially occurs during addition in portions, disappearing again in consequence of the etherification reaction or dissolution. The next glycose portion is preferably not added until the clouding has disappeared. Where the glycose is added continuously, slight clouding of the reaction mixture occurs throughout the entire addition because small quantities of unreacted glycose are always present. In this case, it is important to insure that the addition rate is controlled in such a way that the degree of clouding remains relatively uniform and, in any event, does not increase or rather in such a way that the clouding disappears quickly on termination of the addition with formation of a clear phase.

The acetalization with the butanol is preferably carried out under light vacuum, i.e. under a pressure of 800 to 950 mbar.

Instead of using n-butanol, other short-chain alkanols or alkanediols of relatively similar molecular size, such as for example propanol, pentanol, hexanol or propylene glycol, can be used for the acetalization reaction. However, n-butanol is the preferred substance by virtue of the sum total of its advantageous properties, such as boiling point, separability from the alcohols, and miscibility of the butyl glycoside with the fatty alcohols.

The glycose has fully reacted, when water of reaction stops being formed. At this time the fatty alcohol, preferably preheated to the reaction temperature is introduced in vacuo into the reaction vessel in an amount from about 5 to 7 tools per mol of glycose in such manner that the butanol liberated can be removed by distillation at the same time.

Suitable fatty alcohols are, in particular, the higher aliphatic, primary alcohols containing from 12 to 18 carbon atoms, preferably saturated and preferably straight-chain alcohol of the type obtainable by the industrial hydrogenation of native fatty acids. Typical representatives of the higher aliphatic alcohols which may be used in the process according to the invention are, for example the compounds n-dodecyl alcohol, n-tetradecyl alcohol, n-hexadecyl alcohol, n-octadecyl alcohol, n-octyl alcohol, n-decyl alcohol, undecyl alcohol, tridecyl alcohol. Since the industrial fatty alcohols usually emanate from natural fat sources, mixtures of technical fatty alcohol s can al so be used as reactants, for example a technical mixture of about 3 parts by weight lauryl alcohol and 1 part by weight myristyl alcohol. Although, in principle, any relatively long-chain alcohol containing a primary alcohol group, i.e. even branched-chain primary alcohols, such as for example the so-called oxoalcohols, is suitable for the reaction. The process is primarily intended for the production of surfactants which can be produced exclusively from renewable raw materials.

Within the context of this invention, reduced pressures of down to 10 mbar are established as the vacuum. Through the synchronous exchange of fatty alcohol for butanol, it is possible to obtain a high volume/time yield because the reaction vessels can be made with relatively small dimensions. It has also been found that the proportion of alkyl monoglycosides in the reaction product can thus be increased. In one preferred variant, this means of adding fatty alcohols is designed in such a way that small quantities of the fatty alcohol, for example 0.5 to 10% by weight of the total fatty alcohol used, are introduced into the reaction with the finely dispersed butanol/glycose suspension. The stabilization of the glucose/butanol dispersion can be improved in this way. After the fatty alcohol has been added, the reaction mixture is generally stirred or otherwise agitated in order to take the tranacetalization reaction to the conversion desired. It is possible to control this process in such manner that less than about 1% by weight butyl glycoside is present. In many cases, however, the end product is required to contain certain proportions of butyl glycoside above 1%.

It has also been found that the presence of butyl glycoside in the end product of the reaction can be of advantage in a number of ways. In one preferred embodiment, the process is controlled in such way that at least 2% by weight and at most 30% by weight butyl glycoside remain in the reaction mixture. This greater amount butyl glycoside in the reaction mixture improves its fluidity, so that the excess of fatty alcohol is easier to remove by distillation. The light color and alkali stability of the end product are also favorably influenced by the presence of butyl glycoside. Finally, the presence of butyl glycoside can also be of advantage in terms of practical application.

In order to obtain the desired content of butyl glycoside, removal of the butanol by distillation and neutralization of the catalyst are preferably separated by an interim period of stirring of up to about 1 hour, under which the reaction mixture is stirred under normal pressure at temperatures of from 100° to 115° C. and more especially at a temperature of 110° C. In this manner, the reaction of the butyl glycoside with the fatty alcohol can be continued under control. The residual butyl glycoside content can be ascertained by determining the quantity of butanol distilled off or by analyses of product samples.

In principle, the catalyst may be neutralized with any organic or inorganic compounds showing an alkaline reaction, provided that the neutralization products do not interfere with subsequent treatment or use of the product. It is preferred to use alkaline compounds whose neutralization products do not impair the filterability of the mildly alkalized (at least pH 10) reaction mixture. Alkaline compounds which do not form any free water of neutralization during the neutralization reaction are particularly preferred. Suitable inorganic and organic alkaline compounds are, for example, calcium hydroxide, magnesium hydroxide, magnesium oxide or carbonate, sodium carbonate, potassium carbonate, sodium methylate or ethylate, magnesium methylate or ethylate, sodium or magnesium propylate or butylate, preferably the magnesium alcoholoates or magnesium oxide, and also the zeolites NaA and NaX or NaA in admixture with calcium hydroxide (ratio 10:i to I: 1), zeolite NaA preferably containing less bound water than corresponds to the equilibrium value.

After addition of the alkaline compound with striring and adjustment of the mildy alkaline pH value of at least pH 8, preferably pH 9 to 10, the reaction mixture is preferably filtered at temperatures of from 80 to 100° C. While standard vacuum filters can be readily used in the laboratory, cloth filters are generally used for filtration on an industrial scale. In a less preferred embodiment of the process, the reaction mixture is not filtered after the neutralization and alkalization step. In this case, both the acidic catalyst and also the alkaline compound for deactivating the catalyst are best selected so that their reaction products in the reaction mixture do not have an adverse effect. In this case, for example, acidic ion exchange resins are less suitable as catalysts, and basic calcium compounds are not suitable as deactivators.

Vacuum distillation techniques should be used for distilling off the excess fatty alcohol. In using such techniques the socalled sump temperature must be kept at levels at which the alkyl glycoside is thermally stable. This means that the sump temperature should not exceed a value of 160° C. In the laboratory, it is possible to use standard vacuum distillation apparatus at a vacuum of about 0.01 mbar. On an industrial scale, removal of the fatty alcohol by distillation is preferably carried out in a two-stage process. In the first stage the fatty alcohol is reduced from 40% to 20% using a thin-layer evaporator or a falling-film evaporator. This first stage is also used to degas the reaction mixture. In a second stage, the remaining fatty alcohol content is reduced to the required end value using a "short-path" evaporator. Based on the end products desired, this end value may be below 0.5% by weight if the product is to be substantially free from fatty alcohol. Where certain fatty alcohol contents are required in the end product, the end value in question can be higher and can be in the range of from 3 to 5% by weight fatty alcohol. For example, it has been found that end products containing more than 2% by weight and preferably 3 to 5% by weight fatty alcohol afford advantages in terms of practical application of the end product.

In respect to the separation of mixtures of temperature-sensitive components of the invention, it can generally be said that falling-film evaporators and, preferably, thin-layer evaporators have been found to be particularly suitable for gentle evaporation under reduced pressure. This suitability resulting from the extremely short residence times at relatively high temperatures can be maintained in evaporators such as these. In the present case, the thin-layer evaporator has been found to be particularly suitable for the removal of the excess fatty alcohol from the alkyl glycosides as the actual product. Thin-layer evaporators are evaporators in which a highly viscous, low-boiling mixture is applied to a heated wall and is mechanically distributed thereon by rotating wiping arms. This forms thin layers or films of liquid which are continuously renewed. The vapors formed flow countercurrent to the film of product and leave the evaporator to pass into an externally arranged condenser. Thin-layer evaporators are generally operated at reduced pressures of only a few mbar and the residence time of the product is generally only a few seconds.

In a two-stage unit, which is the type preferably used in the process according to this invention, the thin-layer evaporator also serves as a pre-degassing stage for the short-path evaporator used in the second stage. Gases, which are dissolved in the viscous liquid, are thus removed from the liquid during the removal of excess fatty alcohol from the reaction product in the thinlayer evaporator.

The short-path evaporators are wiped-film evaporators having a condenser built into the evaporator. Evaporators of this type are suitable for the distillation of high-boiling, temperature-sensitive products at pressures in the range from $10^{-1}$ to $10^{-4}$ mbar. In short-path evaporators just as in thin-layer evaporators, the liquid is mechanically distributed over the heating surface by wipers. It has been found that excess alcohol can be reduced to virtually any residual level below 1% in the short-path evaporator of the second stage. The two-stage arrangement of the thin-layer evaporator and short-path evaporator provides high throughputs and closely controlled levels of residual fatty alcohol in the end product. For technical purposes, thin-layer and short-path evaporators may be made of such size that throughputs of up to 300 kg/m2/hour, based on the thin-layer evaporator, are possible. It is preferred to use the two stage unit in this preferred process variant according to the invention.

After the alkyl glycoside product has been stripped of excess fatty alcohol, and cooled, the end-product is usually a pale yellowish wax-like mass. This end product i s preferably converted into an aqueous paste having an alkyl glycoside end-product content of about 60%. This aqueous paste is easier to handle. In special cases where the end product must be essentially color-free the aqueous paste can be bleached with hydrogen peroxide or with a suitable organic per acid, such as dodecanedioic per acid. However, if the process according to the invention is properly conducted, there is generally no need to bleach the end product.

The present invention also relates to certain alkyl glycoside mixtures as new products which are prepared by the process described and claimed herein. The product claimed in its broadest sense is a surface-active alkyl glycoside species in which the quantity of alkyl monoglycoside, based on the total quantity of alkyl monoglycoside and alkyl oligoglycoside, is above 70% by weight, preferably between 70 and 90% by weight and more preferably between 75 and 90% by weight. The total quantity of alkyl monoglycoside and alkyl oligoglycoside is made up in such a way that, mathematically, the mean degree of oligomerization is at most 1.35. The alkyl glycoside contains as another essential component polyglycoses, i.e. the new product consists essentially of the three components alkyl monoglycoside, alkyl oligoglycoside and polyglycose.

In the present case, the expression "the product consists essentially of three components" means that, on the one hand, the proportion of short-chain alkyl glycosides, such as butyl glycoside, has been reduced to such extent that less than 1% by weight is present in the product and that the fatty alcohol has been reduced to such extent that less than 0.5% by weight thereof remains in the product. Alkyl oligoglycosides in the present context are alkyl diglycosides, alkyltriglycosides and higher homologs which can be clearly identified by standard analytical techniques. In the products produced by the process according to the invention, these alkyl oligoglycosides consist essentially of the di- and triglycoside compounds only. The third component consists of polyglycoses which are formed by condensation of the glycose molecules with one another in a secondary reaction of the alkylation reaction. The average molecular weight of these polyglycoses is in the range of from 2000 to 10,000. It has surprisingly been found that the presence of these polyglycoses does not affect the storability and alkali stability of the product and that, in addition, the surfactant effect of the alkyl glycoside, i.e. the mixture of alkyl monoglycoside and alkyl oligoglycosides, is not reduced.

Preferably, the alkyl glycoside mixture consists essentially of the three-component combination of 50 to 95% by weight and preferably 65 to 91% by weight alkyl monoglycoside, 2 to 25% by weight and preferably 4 to 20% by weight alkyl oligoglycoside and 5 to 30% by weight and preferably 5 to 25% by weight polyglycose.

In another preferred embodiment, the product according to the invention comprises a four-component combination consisting essentially of: from 45 to 90% by weight and preferably 50 to 90% by weight alkyl monoglycoside, from 2 to 22% by weight and preferably 3 to 20% by weight alkyl oligoglycoside, 4 to 25% by weight polyglycose and 3 to 30% by weight butyl glycoside.

In this case, too, the expression "consisting essentially of" is intended to mean that excess fatty alcohol has been removed substantially completely, i.e. to contents of less than 0.5% by weight, by distillation. In this case, too, the total quantity of alkyl monoglycoside and alkyl oligoglycoside is made up in such a way that, mathematically, the mean degree of oligomerization is at most 1.35. The preferred glycose of the product is glucose, although isomerization products which do not belong to the essential constituents may also be present in small quantities.

Finally, another preferred form of the alkyl glycoside mixture comprises a five-component combination containing as the fifth component 0.5 to 5% by weight and preferably 2.5 to 4% by weight fatty alcohol, the other four essential components being present in a correspondingly reduced quantity. In many cases, an essential content of free fatty alcohol containing 12 to 18 carbon atoms may be desirable in the interests of practical application. The easiest way of establishing the fatty alcohol content is to terminate the removal of the excess fatty alcohol by distillation at the particular final quantity required.

The quantity of excess fatty alcohol in the end products was determined by gas chromatography. The alkyl monoglucoside and alkyl oligoglucoside contents were determined either by highperformance liquid chromatography (HPLC) or by gas chromatography (GC). In gas chromatography, the peaks were assigned by coupling with a mass spectrometer and comparison with standard substances. In HPLC, the peaks were assigned by fractionation and NMR-spectroscopic identification of the fractions and by comparison with standards. The proportions of polyglucose were isolated by preparative HPLC. The components thus isolated were analytically identified by NMR spectroscopy and by enzymatic sugar tests. The molecular weight range of the polyglucose was determined by gel permeation chromatography (GPC). Secondary products, which can be formed for example by isomerization of the glucose to fructose or by reaction of the fatty alcohols among themselves, and the salts formed by neutralization of the acidic catalyst were not closely identified,

EXAMPLES

The following Examples were all carried out with glucose as the preferred glycose. In most of the Examples, the glucose was used in anhydrous commerically available form. However, it is also believed possible to use dextrose containing 1 mol water.

EXAMPLE 1

This Example describes the process according to the invention using anhydrous glucose on a laboratory scale.

Normal butanol in a quantity of 222 g (3 mol) was introduced into a 2-liter multiple-necked flask equipped with a stirrer, thermometer, dropping funnel and distillation column for the separation of water, followed by addition of 2.2 g (11.2 retool) para-toluenesulfonic acid as catalyst. The mixture was heated to 110° C. A suspension of 180 g (1 mol) anhydrous glucose in another 22 g (3 mol) normal butanol was then added in portions, more specifically in 10 portions, at intervals of 5 minutes. A clear reaction mixture was formed. During the addition, most of the water of reaction formed was distilled off together with butanol under normal pressure (quantity of distillate: 90.7 g, water content 14.3%, as determined by the Karl Fischer method). 1164 g (6 mol) of a $C_{12}$–$C_{14}$ fatty alcohol (mixture tetradecanol) preheated to around 80° C. were then continuously added to the reaction mixture over a period of 75 minutes, more butanol being distilled off at the same time. To this end, the pressure was first adjusted to 800 mbar and then gradually reduced to 10 mbar (quantity of distillate 334 g). After the butanol had been distilled off, the mixture was stirred for 30 minutes at 110° C./normal pressure and then cooled to 90° C. The catalyst was then deactivated by addition of 1.93 g (16.9 mmol) magnesium ethylate with stirring over a period of 90 minutes at 90° C. The reaction mixture then had a pH value of 9–10. After filtration at 90° C. through a heated vacuum filter, the product was distilled in vacuo at 0.01 mbar and at a maximum sump temperature of 160° C. to separate off the excess fatty alcohol. The quantity of distillate amounted to 1044 g and the distillation residue, i.e. the end product, to 298 g. This residue was processed with water at 70 to 80° C. to form a 60% paste.

Characteristic product data: OH value 691; acid value 2.0; residual fatty alcohol 3.1% by weight; butyl glucoside 18.0% by weight; dodecyl/tetradecyl monoglucoside 54% by weight; dodecyl/tetradecyl oligoglucoside (mainly maltoside) 3.5% by weight; polyglucose approx. 20% by weight (MW approx. 2500). These values were determined by HPLC methods.

Color values of the product (40% in water/isopropyl alcohol): Lovibond color values 6 (yellow); 1.4 (red). 0.5% H202 (based on the product) in the form of a 35% solution was added to a sample of the aqueous paste, followed by stirring for 1 hour at 80° C. A pH value of approximately 8 was adjusted by addition of NaOH. Lovibond color values after bleaching: 0.8 (yellow); 0.3 (red).

EXAMPLE 2

This Example describes the process using aqueous glucose.

The reaction mixture and procedure were as in Example 1, except that 189 g dextrose (glucose containing 1 mol water) was used as the glucose. Apart from the fact that the additional quantity of water of approximately 18 g was distilled off during the acetalization with butanol, no significant differences were observed in relation to Example 1.

EXAMPLE 3

This Example describes the stopability and alkali stability test of the product prepared in accordance with the invention.

A 60% aqueous paste of the product was adjusted to pH 12–13 with concentrated NaOH and heated for 0.5 h to 100° C. After cooling to room temperature, an active substance content of 40% by weight (product quantity) was adjusted by addition of isopropyl alcohol. The Lovibond color values (red and yellow) were then measured. A 1 inch cell was used (cf. DGF-Einheitsmethoden, Abteilung C, Fette, C-IV 46 (52), Wissenschaftliche Verlagsgesellschaft mbH, Stuttgart, 1984).

The product of Example 1 was treated by this method. The Lovibond color values were then measured at 18 (yellow) and 3 (red).

Performance tests with the product of Example 1 showed that the product according to the invention with this color quality as a property determined by the above test is adequate for most applications.

The alkali stability test was also conducted with the bleached product of Example 1. Unchanged Lovibond color values of 0.8 (yellow) and 0.3 (red) were then measured. The particularly alkali-stable bleached product is suitable for those applications where the whiteness of a formulation has to satisfy stringent demands.

EXAMPLE 4

This Example describes the working of the process on a production scale.

The following quantities of materials were used:
Mixture of dodecyl and tetradecyl alcohol (Lorol S):1620 kg
Butanol: 871 kg
Papatoluene sulfonic acid: 3.5 kg
Magnesium methylate: 2.0 kg
Glucose (anhydrous) (Pupidex, fine-grained): 250 kg Half the quantity of butanol was initially introduced together with the catalyst into a reaction unit consisting of a 3.2 m$^3$ reactor equipped with a distillation column and an external liquid circuit of a pump and a heat exchanger. A suspension of the glucose in the rest of the butanol was then finely dispersed in a stator/rotor mixer (of the Supraton type), the suspension undergoing an increase i n temperature to 75° C. The glucose/butanol suspension was added continuously over a period of 1.3 hours, during which 65 kg of a butanol/water mixture were distilled off under a reduced pressure of 900 mbar. The energy required for removing this mixture and for maintaining the reaction temperature was provided by an external liquid circuit consisting of a pump and a heat exchanger through which the reaction was passed. The water-saturated butanol phase obtained after phase separation of the butanol/water mixture was returned to the head of the column. After the formation of the butyl glycoside, 725 kg free butanol were present in the reaction mixture after formation of the butyl glycoside, the fatty alcohol preheated to the reaction temperature was continuously added under a reduced pressure of 800 to 10 mbar and, at the same time, the butanol released was separated off, A total reaction time of 1.8 hours was required for the butanol/fatty alcohol exchange reaction and for removal of the residual butanol by distillation, Following an after-reaction time of 1 hour at 110° C. under a pressure of 1013 mbar, the mixture was cooled to 90° C. and the magnesium ethyl ate subsequently added to deactivate the catalyst, After 30 minutes, a pH value of the reaction mixture of 8,5 was measured, After filtration at 85° C. through a bag filter, 1885 kg of the reaction mixture were introduced into a thin-layer evaporator of the Sambay type (0.75 m$^2$ evaporator surface, 8 mbar, approx. 170° C.) and the excess fatty alcohol separated off to a depletion value of approximately 32%. The product kept at 135° C. was low in viscosity and could readily be transferred to a short-path evaporator with roller wipers of the Leybold KD 75 type, The short-path evaporator was operated under the following conditions: evaporator surface 0.75 m$^2$; working pressure 0.075 mbar, as measured in the evaporator; heating temperature 160° C.; sump outflow temperature 152° C. After leaving the short-path evaporator, the product weighed 436 kg; fatty alcohol content 4.9% by weight. Lovibond color values (of the 40% product); 5.5 (yellow) and 1.3 (red). Composition of the product (as determined by GC and HPLC): monoglucoside 55% by weight, oligoglucosides 18% by weight, polyglucose 8% by weight, butyl glucosides 12% by weight, fatty alcohol 3% by weight.

We claim:

1. A transacetalization process for the production of surface active alkyl glycosides containing $C_{12}$ to $C_{18}$ alkyl or alkenyl groups wherein the quantity of alkyl monoglycoside, based on the total quantity of alkyl monoglycoside and alkyl oligoglycoside, is above 70% by weight, which consists essentially of:
   (1) introducing to a reaction vessel from about 30 to about 70 weight percent of the required butanol together with an acidic catalyst:
   (2) heating the butanol-acidic catalyst mixture to the reflux temperature:
   (3) adding a finely-dispersed suspension of a glycose reactant in the remaining butanol at a rate so that the reaction mixture remains substantially clear;

(4) removing the water formed in the reaction by distillation;

(5) adding to the reaction mixture in vacuo a fatty alcohol containing from 12 to 18 carbon atoms;

(6) removing butanol from the reaction mixture by distillation under reduced pressure until from about 0 to about 30 mol percent of butyl glycoside per mol glycose remains in the reaction mixture;

(7) cooling the reaction mixture to a temperature below 95° C. and neutralizing the acidic catalyst by the addition of an inorganic alkaline earth base material and adjusting the pH to at least about 8; and (8) removing excess fatty alcohol by vacuum distillation to a level below about 5% by weight.

2. The process of claim 1 wherein the acidic catalyst is para toluene sulfonic acid.

3. The process of claim 1 wherein in step (1) the first portion of butanol is about 50% of the total amount of butanol which is between about 4 and about 10 mols per mol of glycose.

4. The process of claim 1 wherein the acidic catalyst used is used in an amount of from about 0.005 to about 0.02 mol per mol of the glycose used.

5. The process of claim 1 wherein in step (3) the remaining butanol and glycose is a preheated suspension and is added such that the reaction mixture remains substantially clear.

6. The process of claim 1 wherein in step (4) the water is removed by distillation under a vacuum of about 800 to about 950 mbar.

7. The process of claim 1 wherein in step (5) the fatty alcohol is added in an amount of from about 2 to about 20 mols per mol of glycose.

8. The process of claim 1 wherein in step (7) the pH is adjusted to about 9–10.

9. The process of claim 1 wherein excess fatty alcohol is reduced to a level below about 0.5% by weight.

10. The process of claim 1 wherein in step (3) the glycose used is finely divided anhydrous glucose.

11. The process of claim 1 wherein in step (8) the excess fatty alcohol is removed in two stages, the first of which is conducted in a thin-layer evaporator to a level of about 40% to about 20% and the second of which is conducted in a short path evaporator to a final value of about 3 to about 5% by weight fatty alcohol.

12. The process of claim 1 wherein in step (8) the excess fatty alcohol is removed in two steps the first of which is conducted in a thin-layer evaporator to a level of about 40% to about 20% and the second is conducted in a short path evaporator to a final value of below about 0.5% by weight fatty alcohol.

13. The process of claim 1 wherein the reaction mixture is filtered prior to removing excess fatty alcohol.

14. The process of claim 13 wherein the reaction mixture is filtered at a temperature of from about 80° C. to about 90° C.

15. The process of claim 1 wherein said alkaline earth base material is selected from the group consisting of magnesium hydroxide, magnesium oxide and magnesium carbonate.

16. The process of claim 1 wherein in step (5) the fatty alcohol is added in an amount of from about 5 to about 7 mols per mol of glycose to provide a product wherein the total quantity of alkylmonoglycoside and alkyloligoglycoside has a mean degree of oligomerisation of up to about 1.35.

* * * * *